(12) United States Patent  
Novello

(10) Patent No.: US 8,314,284 B1
(45) Date of Patent: Nov. 20, 2012

(54) DIAPER CHANGE ALERTING MEANS

(76) Inventor: John Novello, East Stroudsburg, PA (US)

( * ) Notice: Subject to any disclaimer, the term of this patent is extended or adjusted under 35 U.S.C. 154(b) by 322 days.

(21) Appl. No.: 12/722,833

(22) Filed: Mar. 12, 2010

(51) Int. Cl.
A61F 13/15 (2006.01)
(52) U.S. Cl. ............... 604/361; 604/385.01; 604/385.19
(58) Field of Classification Search .................. 604/361, 604/385.01, 385.19
See application file for complete search history.

(56) References Cited

U.S. PATENT DOCUMENTS

| 4,106,001 | A | 8/1978 | Mahoney |
| 4,484,573 | A | 11/1984 | Yoo |
| D342,569 | S | 12/1993 | Rasfeld |
| 5,570,082 | A | 10/1996 | Mahgerefteh et al. |
| 5,760,694 | A * | 6/1998 | Nissim et al. ................. 340/604 |
| 5,838,240 | A | 11/1998 | Johnson |
| D423,955 | S | 5/2000 | Mohammed et al. |
| 6,097,297 | A | 8/2000 | Fard |
| 6,603,403 | B2 | 8/2003 | Jeutter et al. |
| 6,870,479 | B2 | 3/2005 | Gabriel |
| 7,145,053 | B1 | 12/2006 | Emenike et al. |

* cited by examiner

Primary Examiner — Jacqueline F. Stephens
(74) Attorney, Agent, or Firm — Kyle Fletcher

(57) ABSTRACT

The diaper change alerting means includes an oblong sensor, speaker, processing means, and powering means. The oblong sensor is positioned about a main portion of the diaper where said sensor can detect the presence of moisture associated with soiling of the diaper. The alerting means can be integrated into the design of a reusable diaper or a removable embodiment that fits within a pouch located about the main portion of a disposable diaper. The processing means receives a signal from the oblong sensor, and transmits an alarm in the form of music via the speaker.

14 Claims, 3 Drawing Sheets

DIAPER CHANGE ALERTING MEANS

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of diapers. More particularly, the present disclosure relates to diapers that have alerting means that emit an alarm upon detection of a dirty diaper.

B. Discussion of the Prior Art

As a preliminary note, it should be stated that there is an ample amount of prior art that deals with diapers. As will be discussed immediately below, no prior art discloses a diaper alerting means that includes an oblong moisture sensor and speaker to emit an audible alarm in the form of music to the presence of soiling of a diaper; wherein the alerting means is integrated into the design of a reusable diaper or from which said diaper has a pouch for installation or removal.

The Gabriel Patent (U.S. Pat. No. 6,870,479) discloses a wetness monitoring system for an infant or adult diaper, which includes a sensor and a monitoring unit with auditory, light, or vibrational alarms. However, the monitoring system requires the use of a monitor with a display as opposed to an alarm system integrated into the system, which is attached to the diaper.

The Jeutter et al. Patent (U.S. Pat. No. 6,603,403) discloses a remote wetness signaling system for a diaper that includes a sensor and an alert signal that can be sent to a remotely located monitor. However, the signaling system is not fully integrated and located in the diaper, but rather includes a wireless receiver for receiving a signal indicating that the diaper has been soiled.

The Rasfeld Patent (U.S. Pat. No. Des. 342,569) illustrates an ornamental design for a wetness indicating diaper, which does not depict a speaker or sensor therein.

The Emenike et al. Patent (U.S. Pat. No. 7,145,053) discloses a baby diaper with a removable moisture indicator that sounds an audible alarm and visual LED lights alerting the diaper is soiled. However, the indicator is selectively attached onto an existing diaper as opposed to integrated into the design of the diaper or by which is removable by a diaper having a predetermined location for the device.

The Johnson Patent (U.S. Pat. No. 5,838,240) discloses a wet diaper detection device that visually and audibly alert parents when a diaper needs to be changed. However, the detector is positioned in a front portion of a diaper, and is attached thereon; whereas the present device is integrated into the diaper or the diaper has a pouch for installation or removal of the device.

The Fard Patent (U.S. Pat. No. 6,097,297) discloses a diaper that has a fastening device that is also a moisture sensor and signal transmitter to a remote receiver to alert a caregiver of a soiled diaper. Again, the device fastens along a side surface of the diaper and is not integrated into a main body portion of the diaper or inserted or removed from a pouch contained about the main body portion of the diaper.

The Mohammed et al. Patent (U.S. Pat. No. Des. 423,955) illustrates a design for a diaper wetness indicator, which does not depict a diaper for use with the indicator.

The Mahgerefteh et al. Patent (U.S. Pat. No. 5,570,082) discloses a sensor for a diaper that sends an alert signal to a remote location when moisture is detected. However, the system utilizes a transmitter to communicate an alarm to a remote location.

The Mahoney Patent (U.S. Pat. No. 4,106,001) discloses a clip-on garment device with a detection strip that is used to alert when a diaper has become soiled. Again, the device fastens along a side surface of the diaper and is not integrated into a main body portion of the diaper or inserted or removed from a pouch contained about the main body portion of the diaper.

The Yoo Patent (U.S. Pat. No. 4,484,573) discloses a diaper that utilizes a buzzer that when the moisture detector indicates moisture is present in the diaper, the detector signals a beeper. However, the detector does not have an oblong shape that extends about a main portion of a diaper from which the detector is integrated or installed/removed from a pouch located there about.

While the above-described devices fulfill their respective and particular objects and requirements, they do not describe a diaper alerting means that includes an oblong moisture sensor and speaker to emit an audible alarm in the form of music to the presence of soiling of a diaper; wherein the alerting means is integrated into the design of a reusable diaper or from which said diaper has a pouch for installation or removal. In this regard, the diaper change alerting means departs from the conventional concepts and designs of the prior art.

SUMMARY OF THE INVENTION

The diaper change alerting means includes an oblong sensor, speaker, processing means, and powering means. The oblong sensor is positioned about a main portion of the diaper where said sensor can detect the presence of moisture associated with soiling of the diaper. The alerting means can be integrated into the design of a reusable diaper or a removable embodiment that fits within a pouch located about the main portion of a disposable diaper. The processing means receives a signal from the oblong sensor, and transmits an alarm in the form of music via the speaker.

It is an object of the invention to provide a diaper change alerting means that senses moisture and emits an alarm in the form of music.

A further object of the invention is to provide a sensor that is oblong in shape so as to provide sensing capabilities about the main portion of the diaper where moisture associated with soiling collects.

A further object of the invention is to provide an alerting means that is either integrated into the design of a reusable diaper or a removable embodiment that can be inserted and removed from a pouch located in a disposable diaper.

A further object of the invention is to provide an alerting means that is powered by a powering means comprising at least one battery.

These together with additional objects, features and advantages of the diaper change alerting means will be readily apparent to those of ordinary skill in the art upon reading the following detailed description of presently preferred, but nonetheless illustrative, embodiments of the diaper change alerting means when taken in conjunction with the accompanying drawings.

In this respect, before explaining the current embodiments of the diaper change alerting means in detail, it is to be understood that the diaper change alerting means is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the diaper change alerting means.

It is therefore important that the claims be regarded as including such equivalent construction insofar as they do not depart from the spirit and scope of the diaper change alerting means. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE EMBODIMENT

Figure 1:
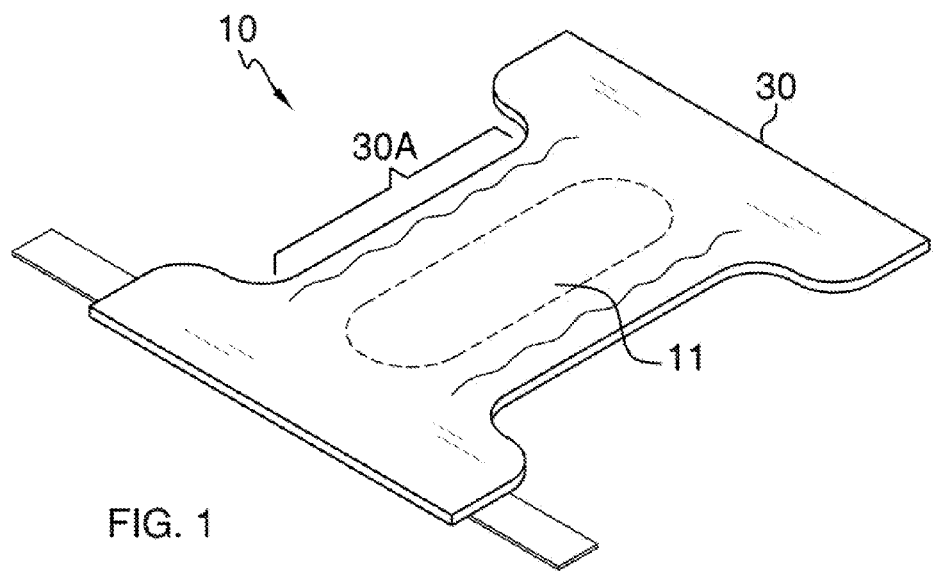
FIG. 1 illustrates a top, isometric view of the diaper change alerting means, and depicting the sensor in dashed lines.
Figure 2:
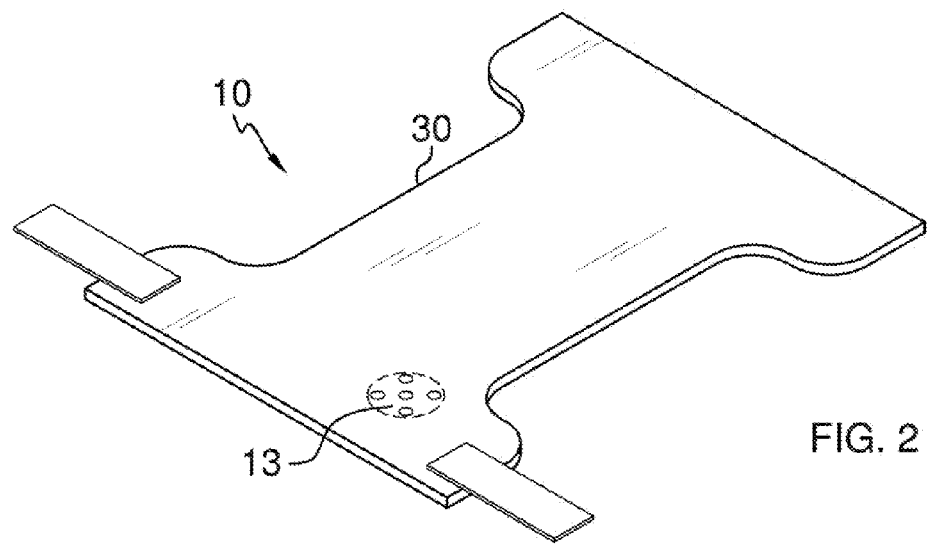
FIG. 2 illustrates a bottom, isometric view of the diaper change alerting means, and detailing the speaker.
Figure 3:
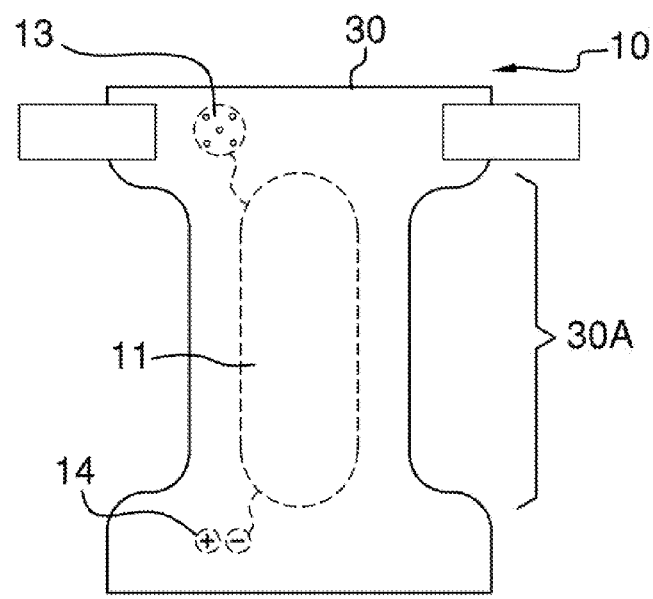
FIG. 3 illustrates a front view of the diaper change alerting means, and detailing the sensor, speaker, and battery(s) in dashed lines.

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to the preferred embodiment of the present invention, examples of which are illustrated in FIGS. 1-4. A diaper change alerting means 10 (hereinafter reusable embodiment) includes an oblong sensor 11, a processing means 12, a speaker 13, and a powering means 14.

The oblong sensor 11 has an elongated shape as the word oblong suggests, and is designed to provide an increased area by which the sensor operates. The oblong sensor 11 senses moisture in order to detect wetness associated with soiling. The oblong sensor 11 is to positioned about a main portion 30A of a diaper 30. The location of the oblong sensor 11 is designed to be more efficient by being located where moisture from soiling collects.

It shall be noted that the diaper 30 is of the reusable ilk, and as such can be cleaned after soiling to reuse the reusable embodiment 10. That being said, the reusable embodiment 10 shall be designed with waterproofing means in mind in order to protect the various electrical components of the reusable embodiment 10. Waterproofing of the reusable embodiment 10 insures adequate sanitation can be achieved between soiling events, and will protect an actual end user from transmission of harmful bacteria or other harmful biological agents, which are associated with soiling materials.

The processing means 12 may also be referred to as a central processing unit (hereinafter CPU). The processing means 12 receives a signal from the oblong sensor 11 via wiring 11A. The processing means 12 in turn emits an alarm 13A via the speaker 13. The alarm 13A ideally will be in the form of music 13B, but may be in the form of a predefined noise, not in the form of music.

The electrical needs of the reusable embodiment 11 are provided by the battery pack 14. The battery pack 14 comprises of at least one battery. The battery pack 14 is responsible for supplying electrical energy to the oblong sensor 11, the processing means 12, and the speaker 13.

Figure 4:
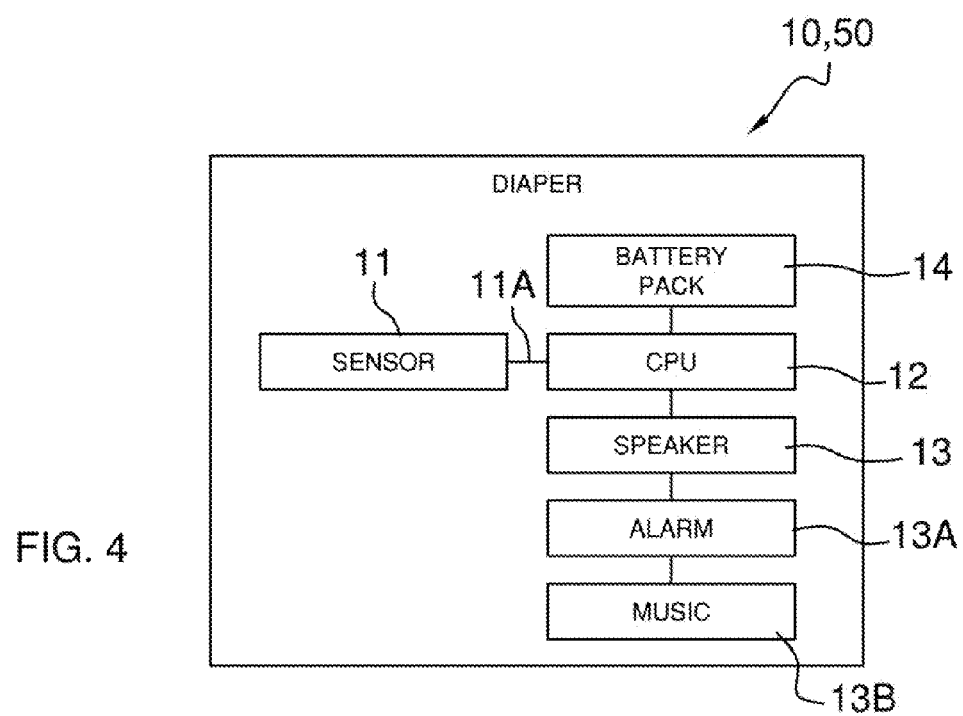
FIG. 4 illustrates a diagram of the various components of the diaper change alerting means.
Figure 5:
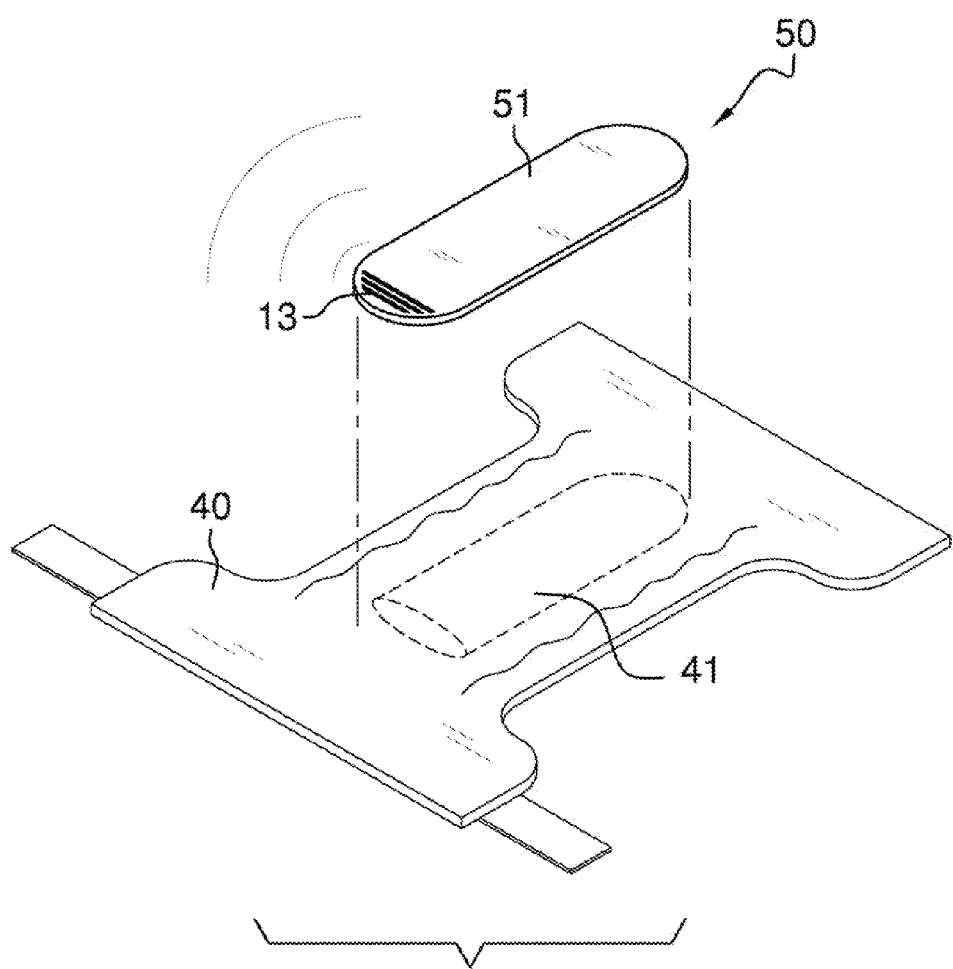
FIG. 5 illustrates an isometric view of an alternative embodiment of the diaper change alerting means wherein the various components are integrated into a device that is removable from the diaper.

Referring to FIGS. 4 and 5, a disposable embodiment 50 includes the same electrical components as the reusable embodiment 10. However, all of the components of the disposable embodiment 50 are contained within a housing 51. The disposable embodiment is designed to fit within a pouch 41 of a disposable diaper 40. The pouch 41 is situated at a main portion of the disposable diaper 40, which is to provide maximum sensing efficiency by enabling the oblong sensor 11 to be positioned where moisture associated with soiling collects.

The pouch 41 shall be of permeable construction so as to allow moisture to penetrate in order to be sensed by the oblong sensor 11. The pouch 41 shall have a small opening 41A that enables the disposable embodiment 50 to be installed or removed from the disposable diaper 40. Upon sensing of moisture by the oblong sensor 11, the disposable embodiment 50 is removed and cleaned before introduction into a new disposable diaper 40.

As with the reusable embodiment 10, the disposable embodiment 50 shall be designed with waterproofing means in mind so as to protect the various electrical components of the disposable embodiment. The housing 51 shall be waterproofed in order to protect the speaker 13, the processing means 12, the oblong sensor 11, and the powering means 14 from damage associated with exposure to water or conductive materials. Waterproofing the disposable embodiment 50 allows the disposable embodiment 50 to be cleaned and sanitized after sensing of moisture associated with soiling agents, which insures that the actual end user will not be exposed to soiling agents during use of a new disposable diaper 40.

It shall be noted that the speaker 13 is located on a side opposite the oblong sensor 11. The speaker 13 shall face an inner surface of the disposable diaper 40, which places the oblong sensor 11 facing moisture passing through the pouch 41.

With respect to the above description, it is to be realized that the optimum dimensional relationship for the various components of the invention 10, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 10.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A diaper change alerting means comprising:
   a sensor that is positioned about a main portion of a diaper, which will sense moisture associated with soiling agents;
   said main portion being a location in said diaper where moisture associated with soiling collects;
   said sensor being fully confined within said main portion, and not extending there beyond;
   a processing means receives a signal from said sensor and emits an alarm;
   a powering means powers the processing means and the sensor;
   wherein the sensor is oblong;
   wherein the sensor is placed facing upwards and away from said main portion of said diaper such that said sensor is able to detect moisture upon impact therewith and in accordance with soiling agents;
   wherein the diaper has a permeable layer that covers the sensor and through which moisture shall pass to engage said sensor.

2. The diaper change alerting means as described in claim 1 wherein the powering means consists of at least one battery.

3. The diaper change alerting means as described in claim 1 wherein the alarm is emitted via a speaker.

4. The diaper change alerting means as described in claim 3 wherein the alarm comprises music or non-musical noise.

5. The diaper change alerting means as described in claim 1 wherein sensor, processing means, and the powering means are integrated into the diaper; and wherein the diaper is reusable.

6. The diaper change alerting means as described in claim 5 wherein the sensor, processing means, and the powering means are waterproofed.

7. A diaper change alerting means comprising:
   a sensor that is inserted and removed from a pouch located about a main portion of a diaper; wherein the sensor will sense moisture associated with soiling agents;
   said main portion being a location in said diaper where moisture associated with soiling collects;
   said sensor being fully confined within said main portion, and not extending there beyond;
   a processing means receives a signal from said sensor and emits an alarm;
   a powering means powers the processing means and the sensor;
   wherein the sensor is oblong;
   wherein the sensor, processing means, and powering means are located within a waterproofed housing.

8. The diaper change alerting means as described in claim 7 wherein the pouch of said diaper has a permeable layer that covers the housing.

9. The diaper change alerting means as described in claim 8 wherein the pouch has an opening for insertion or removal of the housing.

10. The diaper change alerting means as described in claim 7 wherein the powering means consists of at least one battery.

11. The diaper change alerting means as described in claim 7 wherein the alarm is emitted via a speaker.

12. The diaper change alerting means as described in claim 11 wherein the alarm comprises music or non-musical noise.

13. The diaper change alerting means as described in claim 7 wherein sensor, processing means, and the powering means are integrated into the diaper; and wherein the diaper is reusable.

14. The diaper change alerting means as described in claim 13 wherein the sensor, processing means, and the powering means are waterproofed.

* * * * *